(12) United States Patent
Askem et al.

(10) Patent No.: US 11,305,047 B2
(45) Date of Patent: Apr. 19, 2022

(54) SYSTEMS AND METHODS FOR DRIVING NEGATIVE PRESSURE SOURCES IN NEGATIVE PRESSURE THERAPY SYSTEMS

(71) Applicant: Smith & Nephew PLC, Watford (GB)

(72) Inventors: Ben Alan Askem, Leeds (GB); Victoria Beadle, Hull (GB); John Philip Gowans, Hessle (GB); Mark Hesketh, Royston (GB); Allan Kenneth Frazer Grugeon Hunt, Beverley (GB); William Kelbie, Inverness (GB); Damyn Musgrave, Cottenham (GB); Joseph William Robinson, Papworth Everard (GB)

(73) Assignee: Smith & Nephew PLC, Watford (GB)

(*) Notice: Subject to any disclaimer, the term of this patent is extended or adjusted under 35 U.S.C. 154(b) by 692 days.

(21) Appl. No.: 16/098,604

(22) PCT Filed: May 3, 2017

(86) PCT No.: PCT/EP2017/060470
§ 371 (c)(1),
(2) Date: Nov. 2, 2018

(87) PCT Pub. No.: WO2017/191158
PCT Pub. Date: Nov. 9, 2017

(65) Prior Publication Data
US 2019/0125943 A1 May 2, 2019

Related U.S. Application Data

(60) Provisional application No. 62/479,592, filed on Mar. 31, 2017, provisional application No. 62/331,109, filed on May 3, 2016.

(51) Int. Cl.
*A61M 1/00* (2006.01)

(52) U.S. Cl.
CPC ............ *A61M 1/74* (2021.05); *A61M 1/90* (2021.05); *A61M 1/962* (2021.05);
(Continued)

(58) Field of Classification Search
CPC ............ A61M 1/74; A61M 2205/3331; A61M 2205/33; A61M 2205/0294; A61M 1/962; A61M 1/80; A61M 1/90–966
See application file for complete search history.

(56) References Cited

U.S. PATENT DOCUMENTS 3,874,387 A 4/1975 Barbieri
4,224,941 A 9/1980 Stivala
(Continued)

FOREIGN PATENT DOCUMENTS

CN 201664463 U 12/2010
DE 19844355 A1 4/2000
(Continued)

OTHER PUBLICATIONS

International Search Report and Written Opinion, re PCT Application No. PCT/EP2017/060470, dated Aug. 4, 2017.
(Continued)

*Primary Examiner* — Susan S Su
(74) *Attorney, Agent, or Firm* — Knobbe, Martens, Olson & Bear, LLP (57) ABSTRACT

Embodiments of negative pressure wound therapy systems and methods are disclosed. In one embodiment, an apparatus includes a source of negative pressure, a coupling circuit, a driving circuit, and a controller. The driving circuit supplies a driving signal to the source of negative pressure via the coupling circuit to cause the source of negative pressure to provide negative pressure to a wound dressing. The coupling circuit includes an inductive reactance that limits a rate of
(Continued)

change over time of the driving signal. The controller controls the driving signal supplied by the driving circuit.

18 Claims, 8 Drawing Sheets

(52) U.S. Cl.
CPC .............. *A61M 2205/0294* (2013.01); *A61M 2205/106* (2013.01); *A61M 2205/33* (2013.01); *A61M 2205/3331* (2013.01); *A61M 2205/502* (2013.01); *A61M 2205/8212* (2013.01)

(56) References Cited

U.S. PATENT DOCUMENTS

| | | | |
|---|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,699,823 B2 | 4/2010 | Haggstrom et al. |
| 7,776,028 B2 | 8/2010 | Miller et al. |
| D625,422 S | 10/2010 | Arbesman et al. |
| 7,815,616 B2 | 10/2010 | Boehringer et al. |
| 7,837,673 B2 | 11/2010 | Vogel |
| 7,846,141 B2 | 12/2010 | Weston |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,080,702 B2 | 12/2011 | Blott et al. |
| 8,092,441 B2 | 1/2012 | Sugito |
| 8,158,844 B2 | 4/2012 | Mcneil |
| 8,167,869 B2 | 5/2012 | Wudyka |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,449,508 B2 | 5/2013 | Coulthard et al. |
| 8,500,776 B2 | 8/2013 | Ebner |
| 8,529,548 B2 | 9/2013 | Blott et al. |
| 8,545,466 B2 | 10/2013 | Andresen et al. |
| 8,579,872 B2 | 11/2013 | Coulthard et al. |
| 8,603,074 B2 | 12/2013 | Kagan |
| 8,604,265 B2 | 12/2013 | Locke et al. |
| 8,641,691 B2 | 2/2014 | Fink et al. |
| 8,641,693 B2 | 2/2014 | Locke et al. |
| 8,702,665 B2 | 4/2014 | Locke et al. |
| 8,764,732 B2 | 7/2014 | Hartwell |
| 8,795,257 B2 | 8/2014 | Coulthard et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,870,837 B2 | 10/2014 | Locke et al. |
| 8,905,985 B2 | 12/2014 | Allen et al. |
| 8,915,895 B2 | 12/2014 | Jaeb et al. |
| 8,961,496 B2 | 2/2015 | Locke et al. |
| 8,974,429 B2 | 3/2015 | Gordon et al. |
| 9,050,209 B2 | 6/2015 | Coulthard et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,198,802 B2 | 12/2015 | Robinson et al. |
| 9,259,558 B2 | 2/2016 | Tsai |
| 9,265,665 B2 | 2/2016 | Robinson et al. |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,452,088 B2 | 9/2016 | Shulman et al. |
| 9,560,975 B2 | 2/2017 | Mei et al. |
| D787,690 S | 5/2017 | Mackay et al. |
| 9,737,649 B2 | 8/2017 | Begin et al. |
| 9,770,368 B2 | 9/2017 | Robinson et al. |
| 9,814,811 B2 | 11/2017 | Aalders et al. |
| 9,907,703 B2 | 3/2018 | Allen et al. |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |
| 10,010,656 B2 | 7/2018 | Jaeb et al. |
| 10,016,544 B2 | 7/2018 | Coulthard et al. |
| 10,046,095 B1 | 8/2018 | Middaugh et al. |
| 10,046,096 B2 | 8/2018 | Askem et al. |
| 10,086,117 B2 | 10/2018 | Locke et al. |

(56) References Cited

U.S. PATENT DOCUMENTS

| | | | |
|---|---|---|---|
| 2003/0014022 A1* | 1/2003 | Lockwood | A61M 1/732 604/315 |
| 2003/0212357 A1 | 11/2003 | Pace | |
| 2004/0076662 A1 | 4/2004 | Riesinger | |
| 2004/0087884 A1 | 5/2004 | Haddock et al. | |
| 2004/0167482 A1 | 8/2004 | Watson | |
| 2005/0012616 A1 | 1/2005 | Forster et al. | |
| 2005/0045461 A1 | 3/2005 | Sweetland et al. | |
| 2005/0065471 A1 | 3/2005 | Kuntz | |
| 2005/0119737 A1 | 6/2005 | Bene et al. | |
| 2005/0137539 A1 | 6/2005 | Biggie et al. | |
| 2006/0029650 A1 | 2/2006 | Coffey | |
| 2006/0086598 A1 | 4/2006 | Sneek et al. | |
| 2006/0107642 A1 | 5/2006 | Smith et al. | |
| 2006/0259102 A1 | 11/2006 | Slatkine | |
| 2007/0055209 A1 | 3/2007 | Patel et al. | |
| 2007/0128055 A1 | 6/2007 | Lee | |
| 2007/0179460 A1 | 8/2007 | Adahan | |
| 2007/0225663 A1 | 9/2007 | Watt et al. | |
| 2007/0255187 A1 | 11/2007 | Branch | |
| 2007/0265586 A1 | 11/2007 | Joshi et al. | |
| 2008/0021356 A1 | 1/2008 | Castello Escude | |
| 2008/0051716 A1 | 2/2008 | Stutz | |
| 2009/0012484 A1 | 1/2009 | Nielsen et al. | |
| 2009/0048556 A1 | 2/2009 | Durand | |
| 2010/0022990 A1 | 1/2010 | Karpowicz et al. | |
| 2010/0100160 A1 | 4/2010 | Edman et al. | |
| 2010/0137775 A1 | 6/2010 | Hu et al. | |
| 2010/0160881 A1 | 6/2010 | Lin et al. | |
| 2010/0280469 A1 | 11/2010 | Hall et al. | |
| 2010/0292632 A1 | 11/2010 | Mulvihill et al. | |
| 2011/0092927 A1 | 4/2011 | Wilkes et al. | |
| 2011/0112492 A1 | 5/2011 | Bharti et al. | |
| 2011/0190670 A1* | 8/2011 | Jaeb | F04B 43/046 601/6 |
| 2011/0224631 A1 | 9/2011 | Simmons et al. | |
| 2011/0288510 A1* | 11/2011 | Locke | A61M 1/74 604/319 |
| 2011/0292623 A1 | 12/2011 | Stanley | |
| 2011/0305736 A1 | 12/2011 | Wieland et al. | |
| 2012/0059294 A1 | 3/2012 | Schubert et al. | |
| 2012/0109034 A1 | 5/2012 | Locke et al. | |
| 2012/0109083 A1* | 5/2012 | Coulthard | A61F 13/0216 604/319 |
| 2013/0215638 A1 | 8/2013 | Dabov et al. | |
| 2014/0100536 A1 | 4/2014 | Angel | |
| 2014/0343518 A1 | 11/2014 | Riesinger | |
| 2015/0057625 A1 | 2/2015 | Coulthard | |
| 2015/0100045 A1* | 4/2015 | Allen | A61M 1/82 604/543 |
| 2015/0202354 A1 | 7/2015 | Wall | |
| 2016/0015873 A1 | 1/2016 | Robinson et al. | |
| 2016/0166438 A1 | 6/2016 | Rovaniemi | |
| 2016/0199546 A1 | 7/2016 | Chao | |
| 2016/0242964 A1 | 8/2016 | Rapp et al. | |
| 2016/0271305 A1 | 9/2016 | Kurihara et al. | |
| 2016/0361473 A1 | 12/2016 | Robinson et al. | |
| 2017/0112974 A1 | 4/2017 | Fujisaki | |
| 2017/0112975 A1 | 4/2017 | Fujisaki | |
| 2017/0127525 A1 | 5/2017 | Schonholz | |
| 2017/0232189 A1 | 8/2017 | Qin et al. | |
| 2017/0296714 A1 | 10/2017 | Locke et al. | |
| 2017/0319761 A1 | 11/2017 | Locke et al. | |
| 2017/0326277 A1 | 11/2017 | Huang | |
| 2017/0368239 A1 | 12/2017 | Askem et al. | |
| 2018/0008760 A1 | 1/2018 | Zilbershlag et al. | |
| 2018/0021178 A1 | 1/2018 | Locke et al. | |
| 2018/0028728 A1 | 2/2018 | Aarestad et al. | |
| 2018/0055977 A1 | 3/2018 | Pratt et al. | |
| 2018/0104393 A1 | 4/2018 | Wu et al. | |
| 2018/0200414 A1 | 7/2018 | Askem et al. | |
| 2018/0272052 A1 | 9/2018 | Locke et al. | |
| 2018/0296397 A1 | 10/2018 | Askem et al. | |
| 2018/0318137 A1 | 11/2018 | Donda et al. | |
| 2018/0318165 A1 | 11/2018 | Donda et al. | |
| 2018/0353771 A1 | 12/2018 | Kim et al. | |
| 2019/0021911 A1 | 1/2019 | Askem et al. | |
| 2019/0142644 A1 | 5/2019 | Askem et al. | |
| 2019/0143007 A1 | 5/2019 | Askem et al. | |
| 2019/0159938 A1 | 5/2019 | Askem et al. | |
| 2019/0192350 A1 | 6/2019 | Gowans et al. | |
| 2019/0282737 A1 | 9/2019 | Beadle et al. | |
| 2020/0022846 A1 | 1/2020 | Beadle et al. | |

FOREIGN PATENT DOCUMENTS

| | | |
|---|---|---|
| EP | 0512543 A2 | 11/1992 |
| EP | 1411874 A1 | 4/2004 |
| EP | 1455701 B1 | 3/2006 |
| EP | 1448261 B1 | 2/2007 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2326295 A1 | 6/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2305325 B1 | 4/2014 |
| EP | 2323712 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |
| EP | 2829287 A1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2346545 B1 | 10/2015 |
| EP | 2438301 B1 | 10/2015 |
| EP | 2802304 B1 | 12/2015 |
| EP | 2852421 B1 | 1/2016 |
| EP | 2410962 B1 | 3/2016 |

(56) References Cited

FOREIGN PATENT DOCUMENTS

| | | | |
|---|---|---|---|
| EP | 2640436 | B1 | 3/2016 |
| EP | 2855937 | B1 | 5/2016 |
| EP | 2433594 | B1 | 6/2016 |
| EP | 2919730 | B1 | 6/2016 |
| EP | 2861869 | B1 | 7/2016 |
| EP | 2945584 | B1 | 7/2016 |
| EP | 2293749 | B1 | 8/2016 |
| EP | 2305327 | B1 | 10/2016 |
| EP | 2467086 | B1 | 10/2016 |
| EP | 2470135 | B1 | 10/2016 |
| EP | 2767305 | B1 | 10/2016 |
| EP | 2282788 | B1 | 12/2016 |
| EP | 2462956 | B2 | 3/2017 |
| EP | 3139878 | A1 | 3/2017 |
| EP | 2249761 | B1 | 4/2017 |
| EP | 1587502 | B1 | 5/2017 |
| EP | 1587554 | B1 | 5/2017 |
| EP | 2731563 | B1 | 5/2017 |
| EP | 2968871 | B1 | 7/2017 |
| EP | 2632613 | B1 | 8/2017 |
| EP | 2781208 | B1 | 8/2017 |
| EP | 2888478 | B1 | 8/2017 |
| EP | 2937107 | B1 | 8/2017 |
| EP | 2967627 | B1 | 8/2017 |
| EP | 3062751 | B1 | 8/2017 |
| EP | 3139879 | B1 | 8/2017 |
| EP | 2359784 | B1 | 9/2017 |
| EP | 3151795 | B1 | 9/2017 |
| EP | 2367518 | B1 | 10/2017 |
| EP | 2675493 | B1 | 10/2017 |
| EP | 3068455 | B1 | 10/2017 |
| EP | 2558046 | B2 | 11/2017 |
| EP | 2736548 | B1 | 11/2017 |
| EP | 3052158 | B1 | 11/2017 |
| EP | 2593058 | B1 | 3/2018 |
| EP | 3139880 | B1 | 3/2018 |
| EP | 1496822 | B1 | 8/2018 |
| EP | 2879633 | B1 | 8/2018 |
| EP | 2227203 | B1 | 9/2018 |
| EP | 2696826 | B1 | 9/2018 |
| EP | 3106186 | B1 | 9/2018 |
| EP | 3162330 | B1 | 9/2018 |
| EP | 3169382 | B1 | 9/2018 |
| EP | 3203953 | B1 | 9/2018 |
| EP | 2941280 | B1 | 10/2018 |
| EP | 3244852 | B1 | 10/2018 |
| EP | 2687241 | B2 | 11/2018 |
| EP | 2687243 | B2 | 11/2018 |
| EP | 3062753 | B1 | 11/2018 |
| EP | 3120879 | B1 | 12/2018 |
| EP | 3191149 | B1 | 1/2019 |
| EP | 2370130 | B1 | 3/2019 |
| EP | 3053609 | B1 | 3/2019 |
| EP | 3180048 | B1 | 3/2019 |
| EP | 3452131 | A1 | 3/2019 |
| EP | 3143974 | B1 | 4/2019 |
| EP | 2285432 | B2 | 6/2019 |
| EP | 3050545 | B1 | 7/2019 |
| EP | 3319656 | B1 | 8/2019 |
| EP | 2355762 | B1 | 9/2019 |
| EP | 2822613 | B1 | 9/2019 |
| EP | 2863855 | B1 | 9/2019 |
| EP | 2482912 | B1 | 10/2019 |
| EP | 3038667 | B1 | 10/2019 |
| EP | 3129095 | B1 | 10/2019 |
| EP | 3191150 | B1 | 10/2019 |
| EP | 3280466 | B1 | 10/2019 |
| EP | 2244756 | B1 | 12/2019 |
| EP | 2968702 | B1 | 12/2019 |
| FR | 2939320 | A1 | 6/2010 |
| GB | 2511523 | A | 9/2014 |
| JP | H04354722 | A | 12/1992 |
| JP | H0870590 | A | 3/1996 |
| RU | 131622 | U1 | 8/2013 |
| WO | WO-2009098696 | A2 | 8/2009 |
| WO | WO 2009/124100 | | 10/2009 |
| WO | WO-2009120951 | A2 | 10/2009 |
| WO | WO-2011130570 | A1 | 10/2011 |
| WO | WO 2011/146535 | | 11/2011 |
| WO | WO-2011135285 | A1 | 11/2011 |
| WO | WO-2011144888 | A1 | 11/2011 |
| WO | WO-2012078723 | A1 | 6/2012 |
| WO | WO-2014099709 | A1 | 6/2014 |
| WO | WO 2015/115516 | | 8/2015 |
| WO | WO 2016/006458 | | 1/2016 |
| WO | WO-2016126560 | A1 | 8/2016 |
| WO | WO-2017079174 | A1 | 5/2017 |
| WO | WO-2017196888 | A1 | 11/2017 |
| WO | WO-2018056060 | A1 | 3/2018 |
| WO | WO-2018115461 | A1 | 6/2018 |
| WO | WO-2018156730 | A1 | 8/2018 |
| WO | WO-2018158250 | A1 | 9/2018 |
| WO | WO-2018162613 | A1 | 9/2018 |
| WO | WO-2018164803 | A1 | 9/2018 |
| WO | WO-2018185138 | A1 | 10/2018 |
| WO | WO-2018192978 | A1 | 10/2018 |

OTHER PUBLICATIONS

International Preliminary Report on Patentability for Application No. PCT/EP2017/060470, dated Nov. 15, 2018, 8 pages.

* cited by examiner

SYSTEMS AND METHODS FOR DRIVING NEGATIVE PRESSURE SOURCES IN NEGATIVE PRESSURE THERAPY SYSTEMS

CROSS-REFERENCE TO RELATED APPLICATIONS

This application claims the benefit of U.S. Provisional Application No. 62/331,109, filed May 3, 2016, and U.S. Provisional Application No. 62/479,592, filed Mar. 31, 2017; the disclosures of which are hereby incorporated by reference in their entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

SUMMARY

In some embodiments, an apparatus for applying negative pressure to a wound is disclosed. The apparatus can include a source of negative pressure, a coupling circuit, a driving circuit, and a controller. The source of negative pressure can provide negative pressure via a fluid flow path to a wound dressing placed over the wound. The source of negative pressure can include an actuator configured to convert an electrical energy to a mechanical energy. The coupling circuit can include an inductive reactance. The driving circuit can supply a driving signal to the actuator via the coupling circuit to cause the source of negative pressure to provide negative pressure. The controller can control the driving signal supplied by the driving circuit.

The apparatus of the preceding paragraph can include one or more of the following features: The actuator can generate negative pressure by converting the electrical energy to the mechanical energy without converting the electrical energy to a magnetic energy. The source of negative pressure can include a piezoelectric pump, and the actuator can include a piezoelectric transducer. The source of negative pressure can include a micropump. The apparatus can further include the wound dressing, and the source of negative pressure can be disposed on or within the wound dressing. The coupling circuit can limit a rate of change over time of the driving signal supplied from the driving circuit to the actuator. The inductive reactance can be greater than 5 mΩ at an operating frequency of 1 kHz. The coupling circuit can include an inductor electrically coupled in series between an output of the driving circuit and an input of the actuator. The inductor can have an inductance between 1 μH and 100 μH. The inductor can have a maximum current rating of at least 1 A. The coupling circuit can include an electrical short electrically coupled in series between another output of the driving circuit and another input of actuator. The driving circuit can include an H-bridge circuit. The controller can further provide a control signal to the driving circuit, and the controller can control the driving signal by adjusting a pulse width modulation of the control signal. A magnitude of the driving signal can be less than 50 V.

A method of operating, using, or manufacturing the apparatus of the preceding two paragraphs is also disclosed.

In some embodiments, a method of operating a negative pressure wound therapy apparatus is disclosed. The method can include: generating and outputting a control signal; activating a plurality of switches responsive to the control signal; supplying a driving signal to an actuator of a source of negative pressure via the plurality of switches; limiting a rate of change over time of the driving signal; and supplying negative pressure with the source of negative pressure to a wound dressing responsive to the driving signal.

The method of the preceding paragraph can include one or more of the following features: The limiting the rate of change over time can include limiting the rate of change over time using an inductive reactance. The supplying negative pressure can be performed by converting an electrical energy to a mechanical energy without converting the electrical energy to a magnetic energy. The activating the plurality of switches can include activating pairs of the plurality of switches responsive to the control signal. The control signal can include a square waveform having a duty cycle of 50%.

BRIEF DESCRIPTION OF THE DRAWINGS

Features and advantages of the present disclosure will be apparent from the following detailed description, taken in conjunction with the accompanying drawings of which.

DETAILED DESCRIPTION

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue oedema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

Overview

A driving circuit of a TNP apparatus can supply a driving signal (for example, an electrical current and voltage) to a negative pressure source of the TNP apparatus via a coupling circuit of the TNP apparatus. The negative pressure source can include a pump like a piezoelectric pump or micropump. The coupling circuit can have an inductive reactance that limits a rate of change over time of the driving signal supplied by the driving circuit to the negative pressure source. Advantageously, in certain embodiments, the TNP apparatus having such a construction may consume less power to generate negative pressure than other TNP apparatuses.

Reduced Pressure Therapy Systems and Methods

Figure 1:
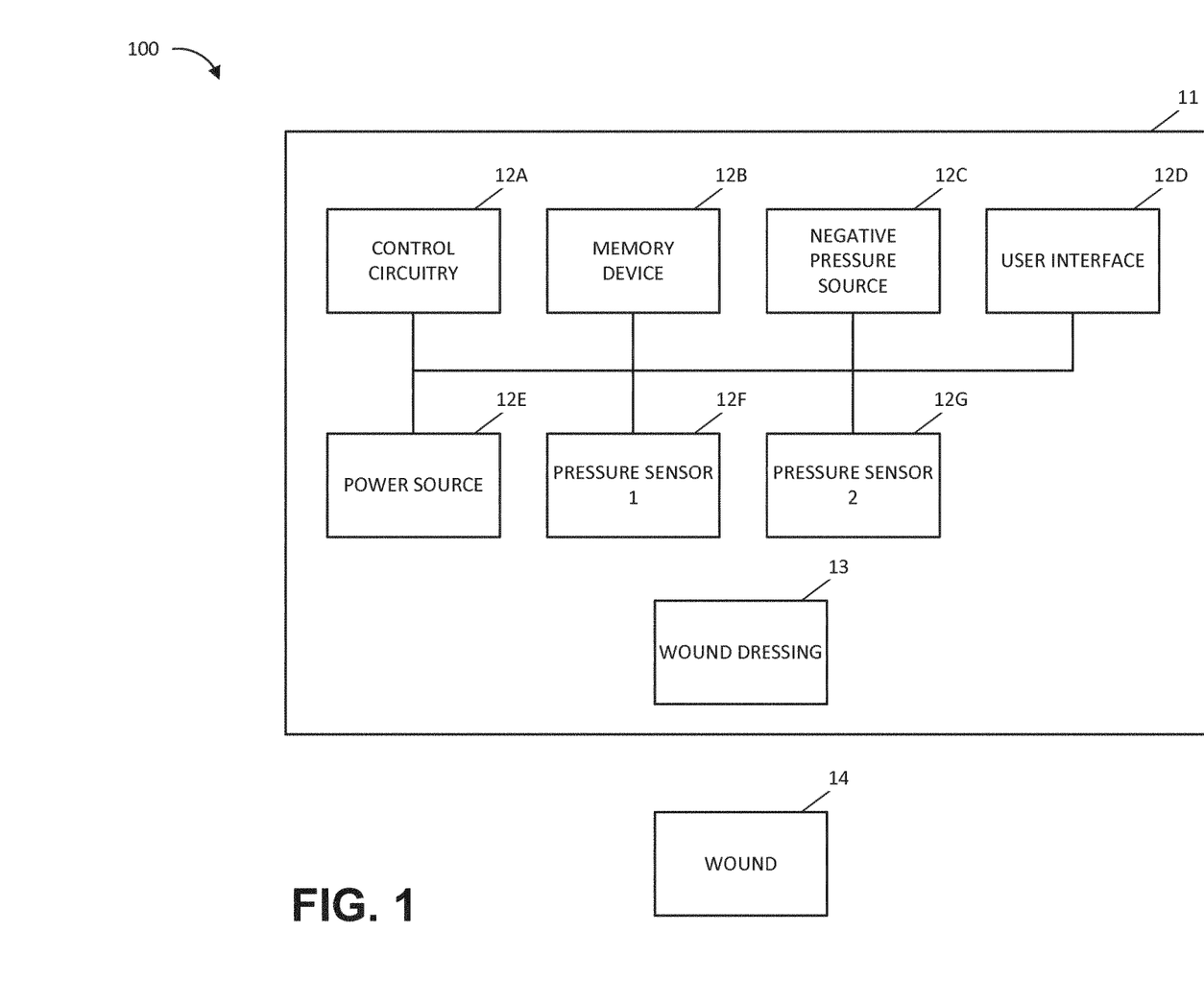
FIG. 1 illustrates a negative pressure therapy system according to some embodiments.

FIG. 1 illustrates a negative pressure therapy system 100 that includes a TNP apparatus 11 and a wound 14 according to some embodiments. The TNP apparatus 11 can be used to treat the wound 14. The TNP apparatus 11 can include control circuitry 12A, memory 12B, a negative pressure source 12C, a user interface 12D, a power source 12E, a first pressure sensor 12F, and a second pressure sensor 12G that are configured to electrically communicate with one another. In addition, the TNP apparatus 11 can include a wound dressing 13. The power source 12E can provide power to one or more components of the TNP apparatus 11.

One or more of the control circuitry 12A, memory device 12B, negative pressure source 12C, user interface 12D, power source 12E, first pressure sensor 12F, and second pressure sensor 12G can be integral with, incorporated as part of, attached to, or disposed in the wound dressing 13. The TNP apparatus 11 can accordingly be considered to have its control electronics and pump on-board the wound dressing 13 rather than separate from the wound dressing 13.

The control circuitry 12A can include one or more controllers (for example, a microcontroller or microprocessor), activation circuits, boost converters, current limiters, feedback conditioning circuits, and H-bridge inverters. The control circuitry 12A can control the operations of one or more other components of the TNP apparatus 11 according at least to instructions stored in the memory device 12B. The control circuitry 12A can, for instance, control operations of and supply of negative pressure by the negative pressure source 12C.

The negative pressure source 12C can include a pump, such as, without limitation, a rotary diaphragm pump or other diaphragm pump, a piezoelectric pump, a peristaltic pump, a piston pump, a rotary vane pump, a liquid ring pump, a scroll pump, a pump operated by a piezoelectric transducer, or any other suitable pump or micropump or any combinations of the foregoing. The pump can include an actuator driven by a source of energy, such as electrical energy, mechanical energy, and the like. For example, the actuator can be an electric motor, a piezoelectric transducer, a voice coil actuator, an electroactive polymer, a shape-memory alloy, a comb drive, a hydraulic motor, a pneumatic actuator, a screw jack, a servomechanism, a solenoid actuator, a stepper motor, a plunger, a combustion engine, and the like. In some embodiments, the negative pressure source 12C can supply negative pressure by converting electrical energy to mechanical energy without converting the electrical energy to magnetic energy. In such embodiments, the negative pressure source 12C can have a different impact when electrically coupled to one or more other components of the control circuitry 12A than if the negative pressure source 12C supplied negative pressure by converting the electrical energy to the magnetic energy and then to the mechanical energy.

The user interface 12D can include one or more elements that receive user inputs or provide user outputs to a patient or caregiver. The one or more elements that receive user inputs can include buttons, switches, dials, touch screens, or the like, and the one or more elements that provide user outputs can include activation of a light emitting diode (LED) or one or more pixels of the display or activation of a speaker or the like. In one example, the user interface 12D can include a switch to receive user inputs (for instance, a negative pressure activation or deactivation input) and two LEDs to indicate an operating status (for example, functioning normally, under fault condition, or awaiting user input) of the TNP apparatus 11.

The first pressure sensor 12F can be used to monitor pressure underneath the wound dressing 13, such as pressure in a fluid flow path connecting the negative pressure source 12C and the wound 14, pressure at the wound 14, or pressure in the negative pressure source 12C. The second pressure sensor 12G can be used to monitor pressure external to the wound dressing 13. The pressure external to the wound dressing can be atmospheric pressure; however, the atmospheric pressure can vary depending on, for instance, an altitude of use or pressurized environment in which the TNP apparatus 11 may be used.

The control circuitry 12A can control the supply of negative pressure by the negative pressure source 12C according at least to a comparison between the pressure monitored by the first pressure sensor 12F and the pressure monitored by the second pressure sensor 12G.

The wound dressing 13 can include a wound contact layer, a spacer layer, and an absorbent layer. The wound contact layer can be in contact with the wound 14. The wound contact layer can include an adhesive on the patient facing side for securing the dressing to the skin surrounding the wound 14 or on the top side for securing the wound contact layer to a cover layer or other layer of the wound dressing 13. In operation, the wound contact layer can provide unidirectional flow so as to facilitate removal of exudate from the wound while blocking or substantially preventing exudate from returning to the wound 14. The spacer layer can assist in distributing negative pressure over the wound site and facilitating transport of wound exudate and fluids into the wound dressing 13. Further, the absorbent layer can absorb and retain exudate aspirated from the wound 14.

The control circuitry 12A can monitor the activity of the negative pressure source 12C, which may include monitoring a duty cycle of the negative pressure source 12C (for example, the duty cycle of the actuator of the negative pressure source). As used herein, the "duty cycle" can reflect the amount of time the negative pressure source 12C is active or running over a period of time. In other words, the duty cycle can reflect time that the negative pressure source 12C is in an active state as a fraction of total time under consideration. Duty cycle measurements can reflect a level of activity of the negative pressure source 12C. For example, the duty cycle can indicate that the negative pressure source 12C is operating normally, working hard, working extremely hard, etc. Moreover, the duty cycle measurements, such as periodic duty cycle measurements, can reflect various operating conditions, such as presence or severity of leaks, rate of flow of fluid (for instance, air, liquid, or solid exudate, etc.) aspirated from a wound, or the like. Based on the duty cycle measurements, such as by comparing the measured duty cycle with a set of thresholds (for instance, determined in calibration), the controller can execute or be programmed to execute algorithms or logic that control the operation of the system. For example, duty cycle measurements can indicate presence of a high leak, and the control circuitry 12A can be programmed to indicate this condition to a user (for instance, patient, caregiver, or physician) or temporarily suspend or pause operation of the source of negative pressure in order to conserve power.

When the TNP apparatus 11 may be used to treat the wound 14, the wound dressing 13 can create a substantially sealed or closed space around the wound 13 and under the wound dressing 13, and the first pressure sensor 12F can periodically or continuously measure or monitor a level of pressure in this space. The control circuitry 12A can control the level of pressure in the space between a first negative pressure set point limit and at least a second negative pressure set point limit. In some instances, the first set point limit can be approximately −70 mmHg, or from approximately −60 mmHg or less to approximately −80 mmHg or more. In some instances, the second set point limit can be approximately −90 mmHg, or from approximately −80 mmHg or less to approximately −100 mmHg or more.

Figure 2A:
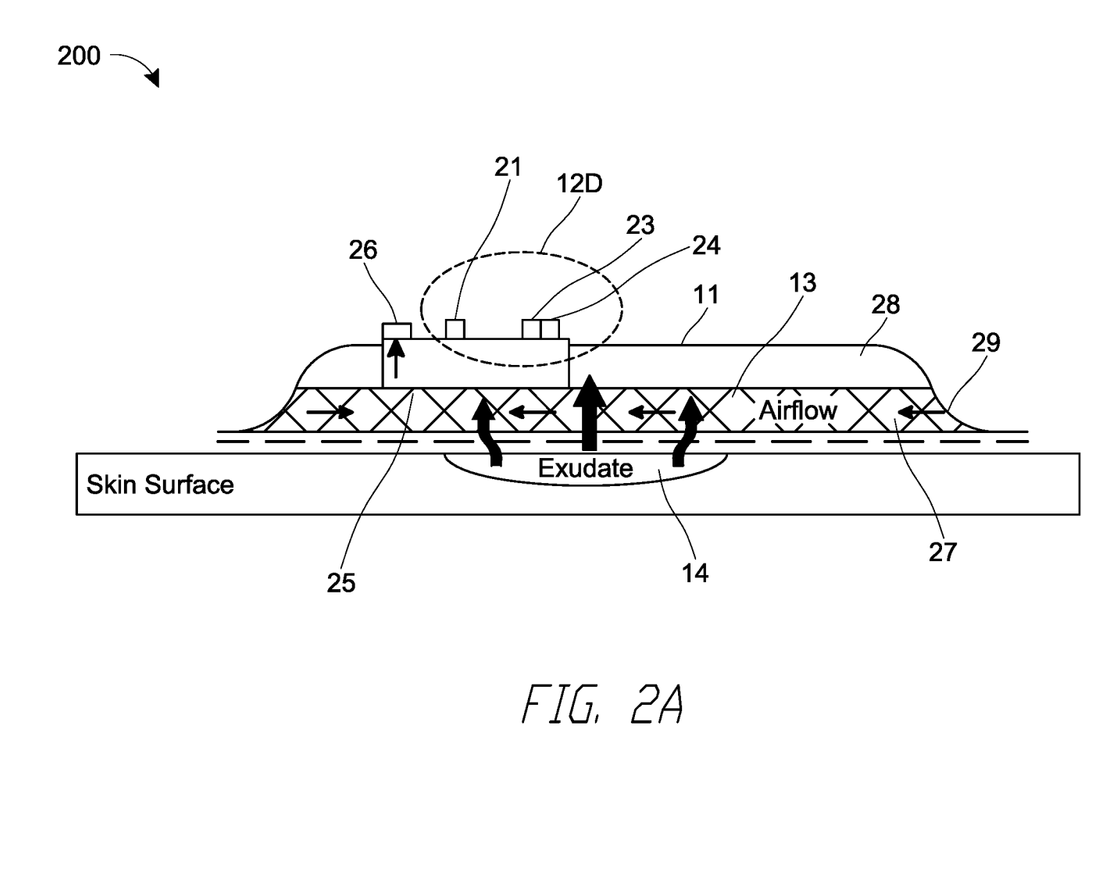
FIGS. 2A and 2B respectively illustrate a side view and top view of a negative pressure therapy system according to some embodiments, such as the negative pressure therapy system of FIG. 1.
Figure 2B:
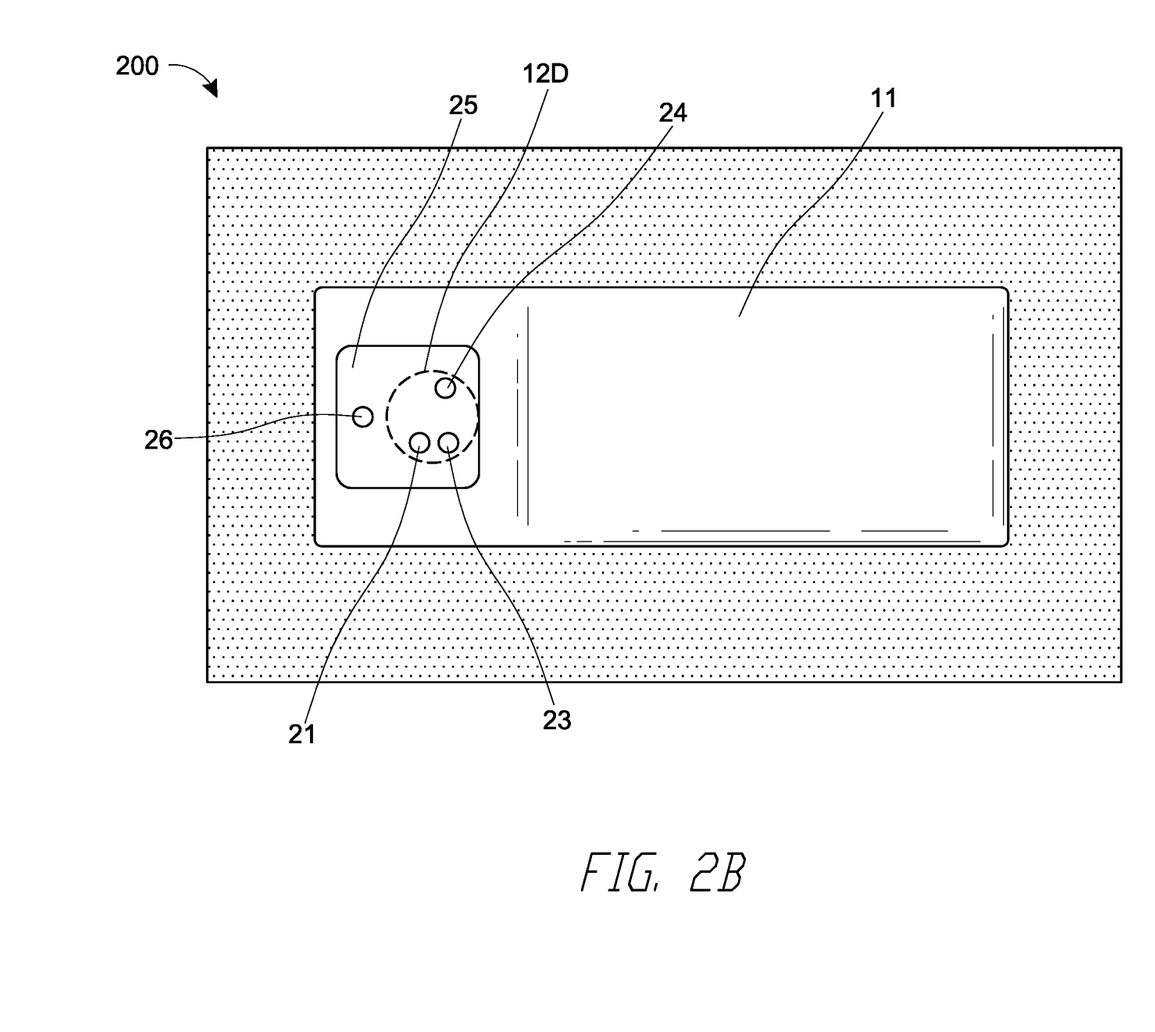

FIG. 2A illustrates a side view of a negative pressure therapy system 200, and FIG. 2B illustrates a top view of the negative pressure therapy system 200 according to some embodiments. The negative pressure therapy system 200 can be an example implementation of the negative pressure therapy system 100.

In the negative pressure therapy system 200, the wound dressing 13 of the TNP apparatus 11 is shown as attached to the wound 14. Arrows depict the flow of air through the wound dressing 13 and wound exudate from the wound 14. The TNP apparatus 11 can include an air exhaust 26 and a component area 25, such as a components housing or storage area for components of the TNP apparatus 11 like one or more of the control circuitry 12A, memory device 12B, negative pressure source 12C, user interface 12D, power source 12E, first pressure sensor 12F, and second pressure sensor 12G.

The user interface 12D of the negative pressure therapy system 200 can include a switch 21 (such as a dome switch), a first indicator 23 (such as a first LED), and a second indicator 24 (such as a second LED). The switch 21 can receive a negative pressure activation or deactivation user input (for example, such as receiving the activation or deactivation user input in response to depression of the switch 21 for a period of time, like from between 0.5 seconds and 5 seconds). The first indicator 23 and the second indicator 24 can indicate an operating status like functioning normally, under fault condition, or awaiting user input. In some implementations, the switch 21 can couple to a power supply connection of the negative pressure source 12C or the control circuitry 12A or an enable signal of the negative pressure source 12C or the control circuitry 12A to activate or deactivate supply of negative pressure or disable supply of negative pressure.

Component parts of the wound dressing 13 of the negative pressure therapy system 200 are illustrated to include an airlock layer 27, an absorbing layer 28, and a contact layer 29. The airlock layer 27 can enable air flow. The absorbing layer 28 can absorb wound exudate. The contact layer 29 can be soft and include silicon and be used to couple the TNP apparatus 11 to the patient.

Figure 3:
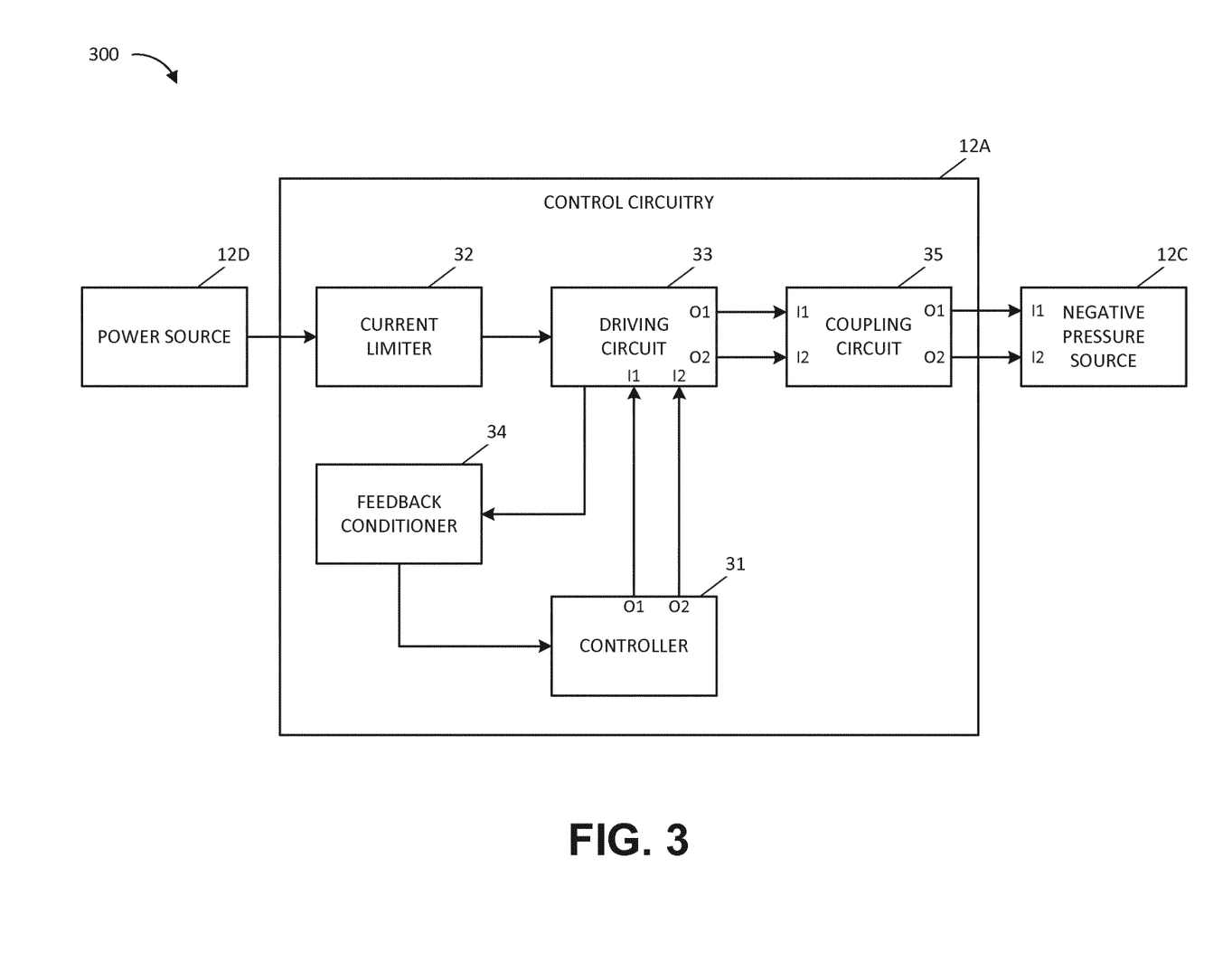
FIG. 3 illustrates a block diagram of electrical communication paths between a power source, control circuitry, and negative pressure source, as well as components of the control circuitry, according to some embodiments.

FIG. 3 illustrates a block diagram 300 depicting example electrical communication paths between the power source 12D, control circuitry 12A, and negative pressure source 12C, as well as example components of the control circuitry 12A including a controller 31, a current limiter 32, a driving circuit 33, a feedback conditioner 34, and the coupling circuit 35. FIG. 3 shows, in particular, how the controller 31 can be used to control the supply of negative pressure by the negative pressure source 12C according to some embodiments.

The power source 12D can include one or more power supplies, such as batteries (such as, multiple 3 V batteries) or a connection to mains power, to provide power for one or more components of the TNP apparatus 11. The power source 12D can, for instance, provide electrical current and voltage to the current limiter 32. The voltage output by the power source 12D can be around 30 V, such as 29 V±1 V, in some implementations. The power source 12D can additionally include circuitry, such as a boost converter, to control the electrical current and voltage provided to the current limiter 32.

The current limiter 32 can serve to limit or clamp the current at a maximum current level, such as at 100 mA, 250 mA, 466 mA, 500 mA, or 1 A, to limit potential fault current through the driving circuit 33 and the negative pressure source 12C. Under normal operation (for example, in most or some instances), the current limiter 32 may not operate to limit current or voltage.

The current limiter 32 can provide electric current and voltage to the driving circuit 33. The driving circuit 33 can include an H-bridge circuit composed of multiple switches. The H-bridge can be constructed to operate as an H-bridge inverter. The driving circuit 33 can provide feedback to the controller 31 via the feedback conditioner 34. The feedback conditioner 34 can be used, for instance, to condition current feedback information from the driving circuit 33 before the current feedback information is provided to the controller 31. In one example, the feedback conditioner 34 can include a low-pass filter (which can, for example, include active circuit components) to filter switching noise caused by the switching of one or more switches of the driving circuit 33. The controller 31 can, in turn, control the operations of the driving circuit 33 based on the feedback, in some instances.

The controller 31 can control operations of the driving circuit 33, and in turn the negative pressure source 12C, by outputting one or more control signals via one or more outputs of the controller 31 to one or more inputs of the driving circuit 33. For example, the controller 31 can output a first control signal via a first output O1 of the controller 31 to a first input I1 of the driving circuit 33 and a second control signal via a second output O2 of the controller 31 to a second input I2 of the driving circuit 33. The controller 31 can vary a pulse width modulation (PWM) of the first and second control signals to adjust an electrical current and voltage provided by the driving circuit 33 to the coupling circuit 35 and then to the negative pressure source 12C. The electrical current or voltage provided by the driving circuit 33 may, in some instances, be referred to herein as a driving signal.

In one implementation, the driving circuit 33 can include an H-bridge, and the controller 31 can generate the first and second control signals to cause the H-bridge to output the driving signal having a square waveform (such as ±3 V, ±5 V, ±10 V, ±15 V, ±20 V, ±25 V, ±30 V, or ±40 V) with a frequency (such as 10 kHz to 32 kHz, 14 kHz to 28 kHz, 18 kHz to 24 kHz, 20 KHz to 22 KHz, or about 21 kHz) and a duty cycle or ratio (such as 20%, 30%, 40%, 45%, 50%, 55%, 60%, 70%, or 80%) via a first output O1 of the driving circuit 33 and a second output O2 of the driving circuit 33.

The driving circuit 33 can control supply negative pressure by the negative pressure source 12C by providing the driving signal to the negative pressure source 12C (for example, to the actuator of the negative pressure source 12C) via the coupling circuit 35. The driving circuit 33 can, for instance, output electrical currents via the first and second outputs O1 and O2 of the driving circuit 33 to a first input I1 of the coupling circuit 35 and a second input I2 of the coupling circuit 35. The coupling circuit 35 can, in turn, output electrical currents via a first output O1 of the coupling circuit 35 and a second output O2 of the coupling circuit 35 to a first input I1 of the negative pressure source 12C and a second input I2 of the negative pressure source 12C. The electrical currents output by the driving circuit 33 and the coupling circuit 35 can notably be considered to result in positive charge flowing away from the driving circuit 33 (that is, sourcing of electrical current by the driving circuit 33) or toward the driving circuit 33 (that is, sinking of electrical current by the driving circuit 33).

The coupling circuit 35 can serve to limit a rate of change over time of the current supplied by the driving circuit 33 to the negative pressure source 12C or limit a rate of change over time of a voltage across first and second inputs I1 and I2 of the negative pressure source 12C. The coupling circuit 35 can have an inductive reactance greater than 1 mΩ, 5 mΩ, 10 mΩ, 50 mΩ, 100 mΩ, 500 mΩ, 750 mΩ at an operating frequency of 1 kHz. In some embodiments, the coupling circuit 35 can include passive circuit elements and not include active circuit elements, but in other embodiments, the coupling circuit 35 can include one or both of passive circuit elements and active circuit elements.

Figure 4A:
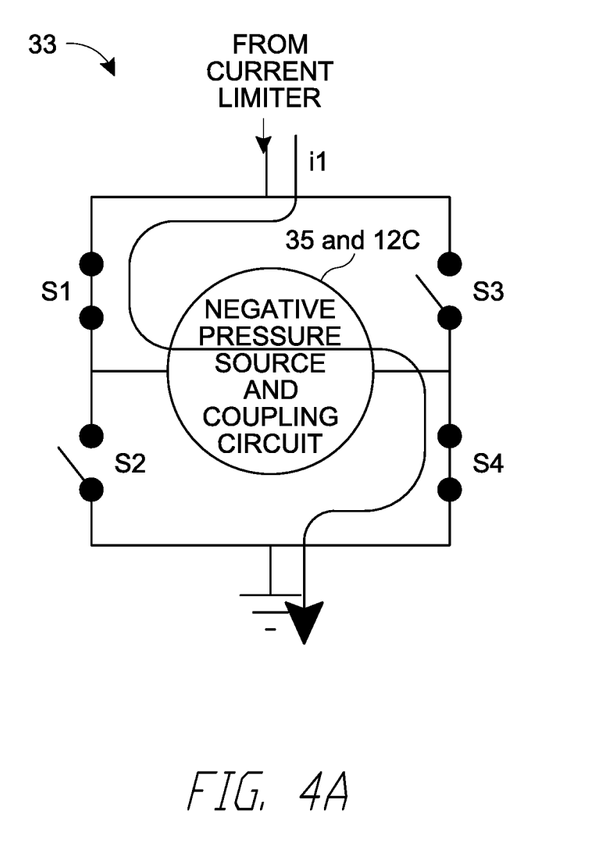
FIGS. 4A and 4B illustrate simplified circuit components of a driving circuit according to some embodiments.
Figure 4B:
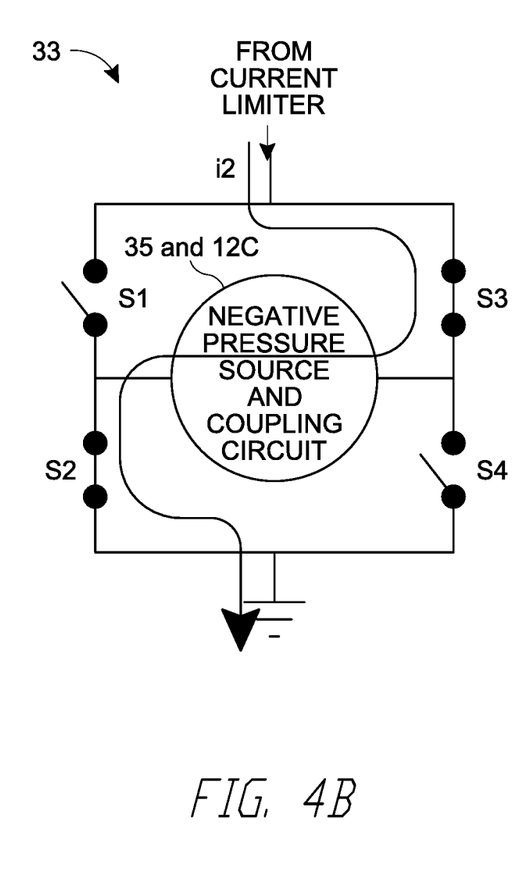

FIGS. 4A and 4B illustrate example simplified circuit components of the driving circuit 33 according to some embodiments. As can be seen from FIGS. 4A and 4B, the driving circuit 33 can be composed of at least four switches, including a first switch S1, a second switch S2, a third switch S3, and a fourth switch S4 but together form an H-bridge. The first and fourth switches S1 and S4 can be closed at the same time and the second and third switches S2 and S3 can be opened at the same time, as shown in FIG. 4A, to supply a first current i1 in a first direction through the coupling circuit 35 and the negative pressure source 12C. The second and third switches S2 and S3 can be closed at the same time and the first and fourth switches S1 and S4 can be opened at the same time, as shown in FIG. 4B, to supply a second current i2 in a second direction through the coupling circuit 35 and the negative pressure source 12C. The first direction can be opposite the second direction.

Figure 4C:
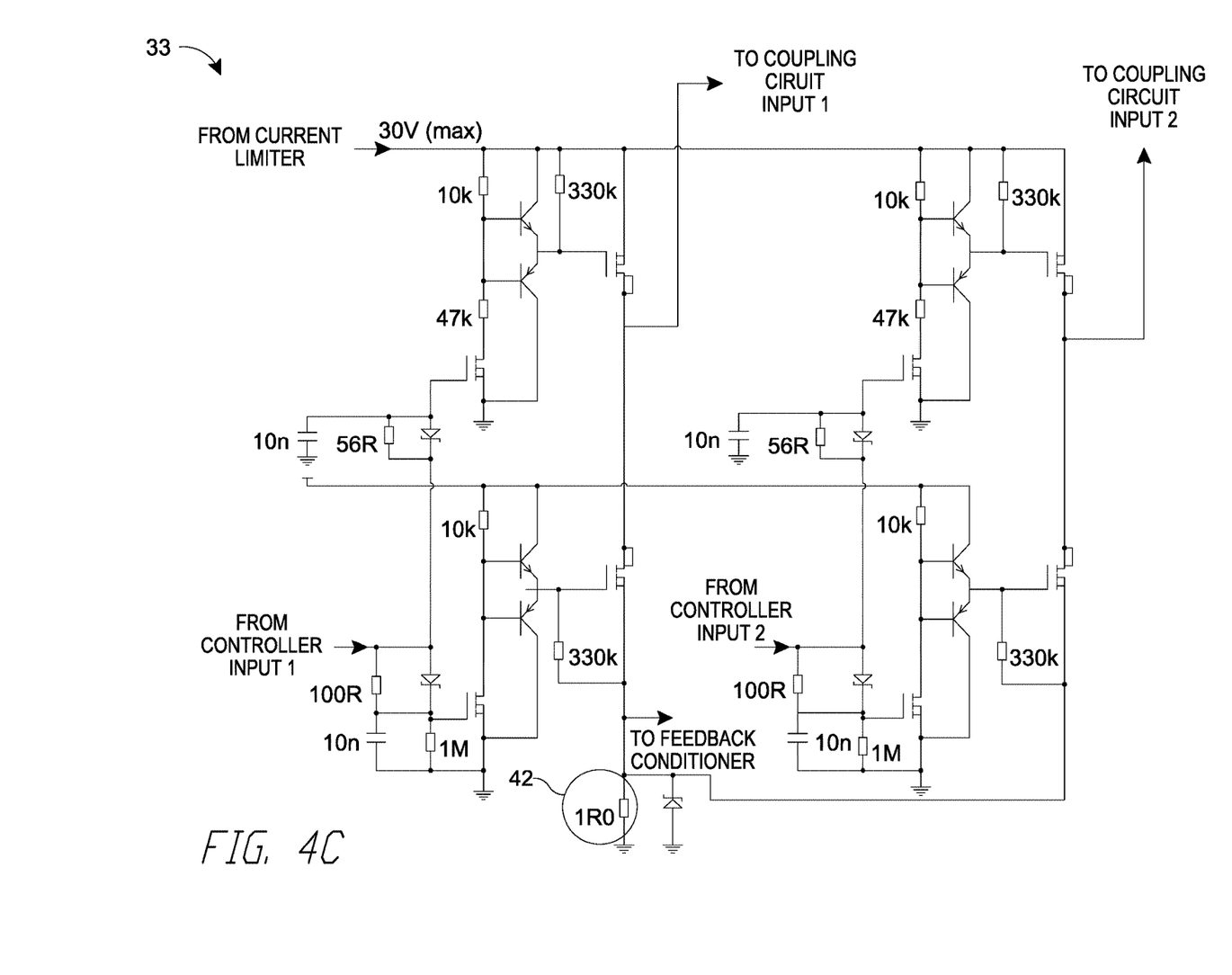
FIG. 4C illustrates circuit components of a driving circuit according to some embodiments.

FIG. 4C illustrates example circuit components of the driving circuit 33 (an H-bridge in the illustrated example) that include a resistor 42 according to some embodiments. In the example circuit components shown in FIG. 4C, the electrical current that travels through the resistor 42 can be the same or substantially the same as the electrical current that travels through the coupling circuit 35 and the negative pressure source 12C (for example, the actuator of the negative pressure source 12C). As a result, a feedback provided to the feedback conditioner 34 can, for instance, be a voltage level or drop across the resistor 42, which can be proportional to the electrical current that travels through the resistor 42, as well as the electrical current that travels through the coupling circuit 35 and the negative pressure source 12C. The resistor 42 thus can be used to measure one or more properties of the electrical current, such as a magnitude, that is fed to the negative pressure source 12C via the coupling circuit 35, such as via an inductor of the coupling circuit 35 like an inductor 52 described with respect to FIG. 5. The resistor 42 can be coupled to a low-pass filter, as described herein.

Figure 5:
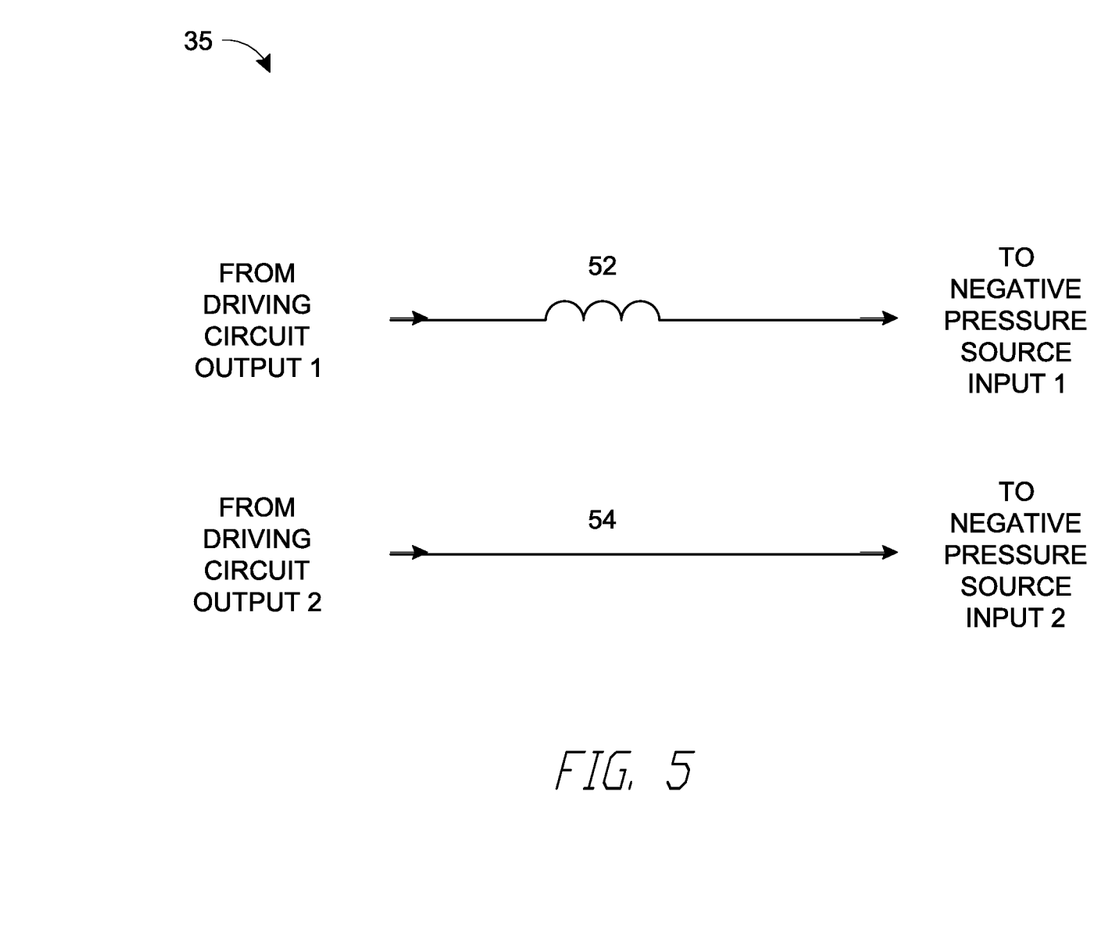
FIG. 5 illustrates circuit components of a coupling circuit according to some embodiments.

FIG. 5 illustrates example circuit components of the coupling circuit 35 according to some embodiments. As can be seen from FIG. 5, the coupling circuit 35 can include (i) the inductor 52 electrically coupled in series between the first output O1 of the driving circuit 33 and the first input I1 of the negative pressure source 12C and (ii) a wire or an electrical short 54 electrically coupled in series between the second output O2 of the driving circuit 23 and the second input I2 of the negative pressure source 12C. The inductor can have an inductance ranging from 0.1 µH to 1000 µH, 1 µH to 100 µH, or 3 µH to 10 µH, or an inductance of about 7.5 µH. The inductor can have a maximum current rating of greater than 0.25 A, 0.5 A, 0.75 A, 1 A, or 1.25 A. The inductor 52 can be used to oppose rapid changes in a current or voltage supplied to drive the negative pressure source 12C.

In another embodiment, the coupling circuit 35 can include (i) a first wire or a first electrical short electrically coupled in series between the first output O1 of the driving circuit 33 and the first input I1 of the negative pressure source 12C and (ii) a second wire or a second electrical short electrically coupled in series between the second output O2 of the driving circuit 33 and the second input I2 of the negative pressure source 12C.

In yet another embodiment, the coupling circuit 35 can include (i) a first wire or a first electrical short electrically coupled in series between the first output O1 of the driving circuit 33 and the first input I1 of the negative pressure source 12C and (ii) an inductor (such as the inductor 52) electrically coupled in series between the second output O2 of the driving circuit 33 and the second input I2 of the negative pressure source 12C.

In yet a further embodiment, the coupling circuit 35 can include (i) a first inductor (such as the inductor 52) electrically coupled in series between the first output O1 of the driving circuit 33 and the first input I1 of the negative pressure source 12C and (ii) a second inductor (such as the inductor 52) electrically coupled in series between the second output O2 of the driving circuit 33 and the second input I2 of the negative pressure source 12C.

In certain implementations, one or more active elements can be used in place of or in addition to one or more inductors.

Figure 6:
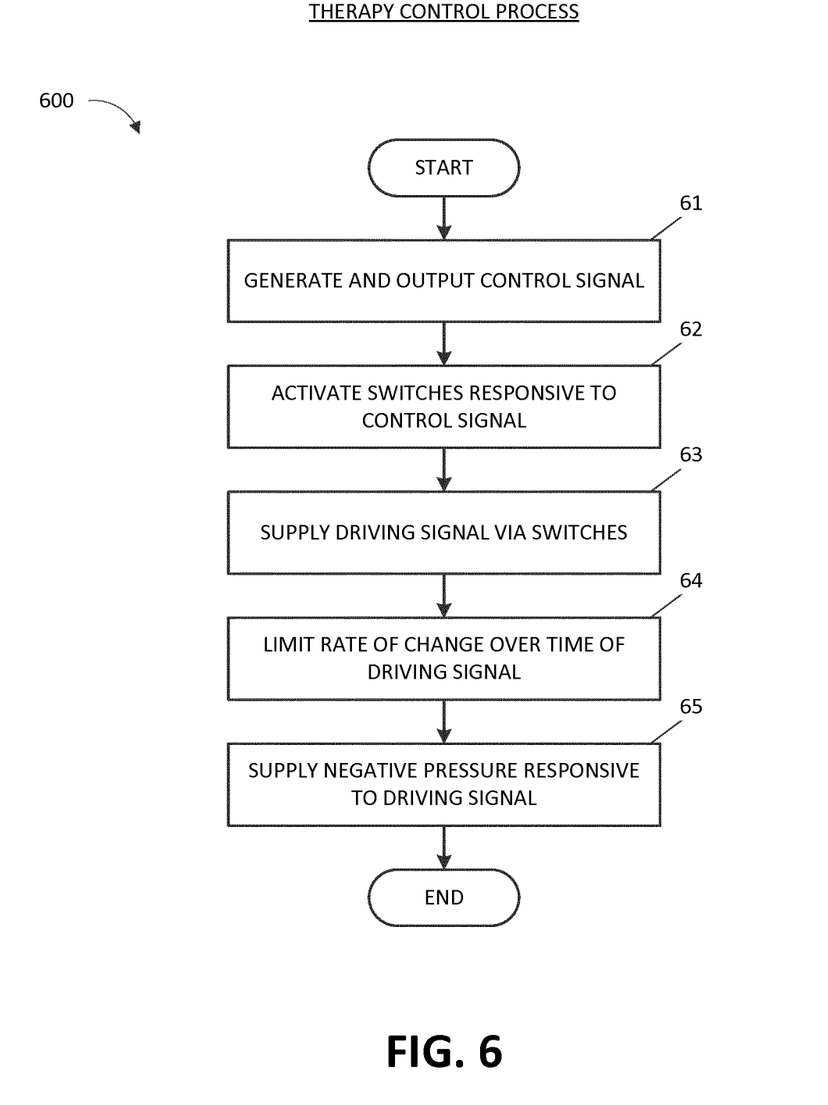
FIG. 6 illustrates a therapy control process performable by a negative pressure therapy system according to some embodiments.

FIG. 6 illustrates a therapy control process 600 performable by an apparatus, such as the TNP apparatus 11 according to some embodiments. For convenience, the therapy control process 600 is described in the context of the TNP apparatus 11, but may instead be implemented in other systems described herein, or by other systems not shown.

At block 61, the therapy control process 600 can generate and output a control signal. For example, the controller 31 can generate and output a control signal to the driving circuit 33. At block 62, the therapy control process 600 can activate switches responsive to the control signal. For example, the driving circuit 33 can selectively open and close one or more switches of the driving circuit 33 responsive to the control signal. At block 63, the therapy control process 600 can supply a driving signal via the switches. For example, the driving circuit 33 can supply the driving signal to the coupling circuit 35 via opening and closing of the one or more switches of the driving circuit 33. At block 64, the therapy control process 600 can limit a rate of change over time of the driving signal. For example, the coupling circuit 35 can limit a rate of change over time of the driving signal from the driving circuit 33 using an inductive reactance. At block 65, the therapy control process 600 can supply negative pressure responsive to the driving signal. For example, the negative pressure source 33 can supply negative pressure to the wound dressing 13 responsive to the driving signal provided by the driving circuit 33 via the coupling circuit 35.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract, and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed:

1. An apparatus for applying negative pressure to a wound, the apparatus comprising:
    a source of negative pressure configured to provide negative pressure via a fluid flow path to a wound dressing placed over a wound of a patient, the source of negative pressure comprising an actuator configured to convert an electrical energy to a mechanical energy;
    a coupling circuit including an inductive reactance;
    a driving circuit configured to supply a driving signal to the actuator via the coupling circuit to cause the source of negative pressure to provide negative pressure; and
    a controller configured to control the driving signal supplied by the driving circuit,
    wherein the coupling circuit comprises an inductor electrically coupled in series between a first output of the driving circuit and a first input of the actuator and an electrical short electrically coupled in series between a second output of the driving circuit and a second input of the actuator.

2. The apparatus of claim 1, wherein the actuator is configured to generate negative pressure by converting the electrical energy to the mechanical energy without converting the electrical energy to a magnetic energy.

3. The apparatus of claim 1, wherein the source of negative pressure comprises a piezoelectric pump, and the actuator comprises a piezoelectric transducer.

4. The apparatus of claim 1, wherein the source of negative pressure comprises a micropump.

5. The apparatus of claim 1, further comprising the wound dressing, the source of negative pressure being disposed on or within the wound dressing.

6. The apparatus of claim 1, wherein the coupling circuit is configured to limit a rate of change over time of the driving signal supplied from the driving circuit to the actuator.

7. The apparatus of claim 1, wherein the inductive reactance is greater than 5 mΩ at an operating frequency of 1 kHz.

8. The apparatus of claim 1, wherein the inductor has an inductance between 1 μH and 100 μH.

9. The apparatus of claim 8, wherein the inductor has a maximum current rating of at least 1 A.

10. The apparatus of claim 1, wherein the driving circuit comprises an H-bridge circuit.

11. The apparatus of claim 1, wherein the controller is further configured to provide a control signal to the driving circuit, and the controller is configured to control the driving signal by adjusting a pulse width modulation of the control signal.

12. The apparatus of claim 1, wherein a magnitude of the driving signal is less than 50 V.

13. The apparatus of claim 1, wherein the driving circuit comprises a boost converter and an H-bridge.

14. A method of treating a wound on a patient, the method comprising:
    by a negative wound therapy apparatus of claim 1:
        generating and outputting a control signal;
        activating a plurality of switches of the driving circuit responsive to the control signal;
        supplying the driving signal to the actuator of the source of negative pressure via the plurality of switches;
        limiting a rate of change over time of the driving signal; and
        supplying negative pressure with the source of negative pressure to the wound dressing responsive to the driving signal.

15. The method of claim 14, wherein said limiting the rate of change over time comprises limiting the rate of change over time using the coupling circuit.

16. The method of claim 14, wherein said supplying negative pressure is performed by converting the electrical energy to the mechanical energy without converting the electrical energy to a magnetic energy.

17. The method of claim 14, wherein said activating the plurality of switches comprises activating pairs of the plurality of switches responsive to the control signal.

18. The method of claim 14, wherein the control signal comprises a square waveform having a duty cycle of 50%.

* * * * *